United States Patent [19]

Butel

[11] Patent Number: 4,516,277

[45] Date of Patent: May 14, 1985

[54] ARTICLE COMPRISING AND METHOD FOR FABRICATING A HIP PROSTHESIS HAVING A FLEXIBLE MULTI-ELEMENT FEMORAL ROD

[76] Inventor: Jean Butel, 19 Avenue de Plain Fleurie, Meylan, Isere, France

[21] Appl. No.: 446,650

[22] Filed: Dec. 3, 1982

[30] Foreign Application Priority Data

Dec. 8, 1981 [FR] France .................. 81 23325

[51] Int. Cl.³ .................. A61F 1/04; B21D 39/00
[52] U.S. Cl. .................. 3/1.913; 29/437; 29/509; 29/DIG. 18; 72/377; 128/92 CA
[58] Field of Search .................. 3/1.91, 1.912, 1.913; 128/92 BC, 92 CA, 92 C; 29/437, 509, DIG. 18; 72/377

[56] References Cited

U.S. PATENT DOCUMENTS

| | | | |
|---|---|---|---|
| 3,848,272 | 11/1974 | Noiles | 128/92 C X |
| 3,996,625 | 12/1976 | Noiles | 128/92 CA X |
| 4,004,300 | 1/1977 | English | 3/1.913 |
| 4,040,129 | 8/1977 | Steinemann et al. | 3/1.91 X |
| 4,156,943 | 6/1979 | Collier | 3/1.913 X |
| 4,172,296 | 10/1979 | D'Errico | 3/1.913 X |
| 4,202,082 | 5/1980 | Williams | 72/377 X |
| 4,266,302 | 5/1981 | Tornier | 3/1.912 |
| 4,287,617 | 9/1981 | Tornier | 128/92 CA X |
| 4,314,381 | 2/1982 | Koeneman | 3/1.912 |

FOREIGN PATENT DOCUMENTS

| | | | |
|---|---|---|---|
| 2425237 | 1/1980 | France | 3/1.913 |
| 2475892 | 8/1981 | France | 3/1.912 |

Primary Examiner—Howard N. Goldberg
Assistant Examiner—Ronald S. Wallace
Attorney, Agent, or Firm—Browdy and Neimark

[57] ABSTRACT

A hip prosthesis comprises a one piece element including a head, a plate portion, a neck interconnecting the head and plate portion, and a flexible femoral rod which includes thin longitudinal elements extending away from the head in opposition to one another. The longitudinal elements are obtained by providing at least a longitudinal cutting in the rod which extends to its end opposite the head. A slot in each end coincident with the cutting houses a linking part for holding the elements together in one plane while permitting their relative movements in a second substantially orthogonal plane. The elements are made in one piece with the head, the neck and the plate of the prosthesis, with the rod itself being forged from a single piece.

19 Claims, 3 Drawing Figures

U.S. Patent
May 14, 1985
4,516,277
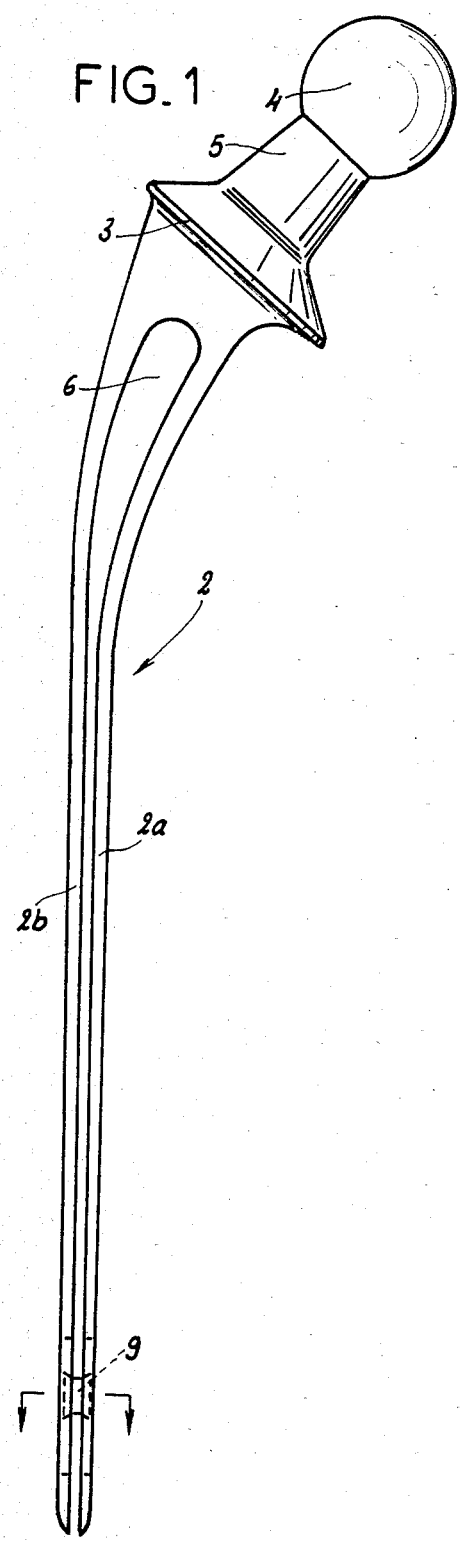
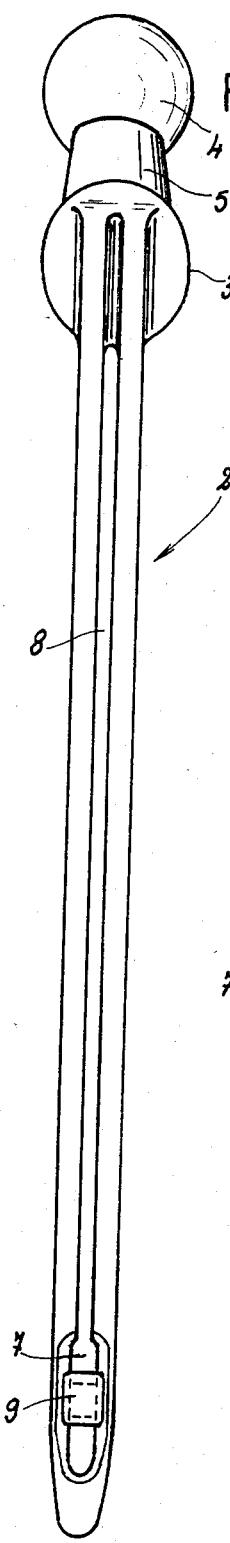
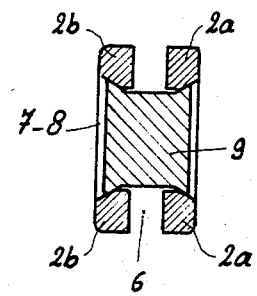

ARTICLE COMPRISING AND METHOD FOR FABRICATING A HIP PROSTHESIS HAVING A FLEXIBLE MULTI-ELEMENT FEMORAL ROD

BACKGROUND OF THE INVENTION

This invention relates to a process for manufacturing a hip prosthesis with a flexible rod, as described in French Pat. No. 2,245,237. This patent relates to a prosthesis of a type comprising an intramedullary femoral rod, a plate formed integral with the rod, a neck inclined relative to the rod and a generally spherical head integral with the neck. The prosthesis is characterized in that it further comprises elastic means able to damp the impacts in the direction of the axis of the femoral rod.

According to a particular embodiment of the prosthesis described in this patent, the femoral rod consists of several thin longitudinal elements, extending from the plate, and the elastic means consist of an end piece integral with at least one of said elements, the other longitudinal elements being able to slide in housings respectively provided for this purpose in said end piece.

In this embodiment, the connection of the longitudinal elements of the rod to the plate is made by welding, which necessitates the presence, on the lower surface of the plate, of a projection against which said elements are applied longitudinally before being attached to it by said welding operation.

SUMMARY OF THE PRESENT INVENTION

The object of this invention is essentially to reduce the production costs of such a prosthesis by simplifying its manufacturing operations and by eliminating the delicate and expensive welding operations and the manufacture and the putting in place of an end piece engaged on its free ends with elements of the rod.

This invention further aims to improve the mechanical characteristics of such a prosthesis.

For this purpose, according to the process to which it relates, the elements of the fasciculate rod are obtained by longitudinal cutting of a rod made in one piece with the head, the neck and the plate, the rod itself being obtained by molding or forging from a single piece; in this way, therefore, the welding operations are totally eliminated.

Preferably, the longitudinal cutting of the rod is performed in two successive operations and in two directions perpendicular to one another, so as to obtain a cluster of four elements arranged in a cross, each cutting operation being performed along the median line of the rod.

Taking into account the direction of the stress to which this prosthesis is subjected, and consequently, the conditions of flexibility that they require, one of the operations for cutting the fasciculate rod is performed along a plane containing the median line and the centers of curvature of the rod of this prosthesis, the other operation being performed along a cylindrical surface perpendicular to said plane and containing the median axis of the rod.

Advantageously, only one of the two cuttings made during said operations, namely the one along the curvature of the rod, emerges at the free end of the rod so that the free ends of the elements of the fasciculate rod located on the same side of this cutting are connected to one another, which does not interfere with the flexibility of the rod by modifying its curvature.

According to another characteristic of the invention, to make possible the total elimination of the end piece for joining the free ends of the elements of the fasciculate rod while allowing the partial solidifying of the free ends of the two pairs of associated elements, on the one hand there is made, in the vicinity of this free end of each pair of elements, a longitudinal slot coinciding with its homologue of the other pair and, on the other hand, there is provided a connecting part that passes through the two slots and is equipped with shoulders preventing the ends of the pairs of elements from moving apart from one another without, however, opposing their axial movement in relation to one another.

BRIEF DESCRIPTION OF THE DRAWINGS

In any case, the invention will be better understood from the description which follows, in reference to the accompanying diagrammatic drawing that represents, by way of nonlimiting example, an embodiment of this prosthesis, wherein:

FIG. 1 is a side view in elevation;

FIG. 2 is a front view in elevation;

FIG. 3 is, on a larger scale, a view along section along 3—3 of FIG. 1.

DETAILED DESCRIPTION OF THE INVENTION

As the drawings show, the prosthesis is of the type having a fasciculate rod 2 intended to be engaged in the medullary canal of the femur, and after resection of the upper end of the latter, a plate 3 is provided to rest against the resectioned end of the femur and a spherical head 4 connected to plate 3 by a neck 5 for resting in the cotyloidal cavity of the hip of the patient either directly, or by cups sealed in this cavity or built up on head 4.

As in French Pat. No. 2,425,237, rod 2 of this prosthesis is a fasciculate rod, i.e., it is composed of longitudinal elements 2a and 2b that give this rod the flexibility necessary to reduce the risks of breaking.

As in the French patent, elements 2a and 2b are integral with plate 3 by their upper ends, while their lower ends enjoy relative independence.

According to the manufacturing process of this invention, elements 2a and 2b which are 4 in number are obtained by two cutting operations made at 90° with respect to each other both along the longitudinal median line of the single-piece rod obtained originally by forging or molding and integral with plate 3, head 4 and neck 5.

As shown in FIG. 1 of the drawing, since a prosthesis for the hip exhibits a certain curvature with several centers located in the same plane, one of the cutting operations is performed in the plane containing both the longitudinal median line of the rod and its centers of curvature, the second cutting operation being performed perpendicular to said plane along the curvature of the median line.

Therefore, four elements are thus obtained, namely two elements 2a and two elements 2b arranged in a cross around the median line of rod 2 and each of these elements is formed integral, at its upper end, with plate 3; thus it is unnecessary to resort to any welding operation.

Taking into account that the flexibility of rod 2 is especially necessary around the centers of maximum curvature on the cutting made in the rod portion adjacent plate 3, cutting 6, seen in FIG. 1, extends to the free end of the rod. The elements of this rod have their lower ends connected to each other, two by two, to form two pairs of elements, namely the pair of elements 2a and the pair of elements 2b, each pair of elements being located on one side or the other of cutting 6.

During the implanting of rod 2 in the medullary canal of the femur of the patient, to prevent the two pairs of elements 2a and 2b from tending to move apart from one another, at each end of a pair 2a and 2b, there is provided a slot 7 that preferably, but need not, communicate with cutting 8 made along the plane containing the median line of rod 2 and its centers of curvature, and a connecting part 9 provided with two end shoulders, serving as rivets and engaged in the two slots 7 which are opposite one another. Of course, linking part 9 is sufficiently long to make possible the longitudinal clearance of the pair of elements 2a in relation to the pair of elements 2b and not to modify the flexibility of rod 2.

It goes without saying that the invention is not limited to the single embodiment of the prosthesis which was described above by way of nonlimiting example; on the contrary, it includes all the variant embodiments of it.

I claim:

1. In a process for making a hip prosthesis including a bulbous head, a neck extending from said head, a plate connected to the neck opposite the head, and a femoral rod attached to, and extending from, the plate in a direction away from the neck, the improvment comprising:
    forging said head, neck, plate and rod as a single unitary piece;
    cutting said rod once along one longitudinally extending portion thereof to form a pair of opposing longitudinal elements; and
    linking said pair of elements with separate holding means, said separate holding means both permitting relative movements of said elements longitudinally of one another during flexing of said elements, and holding said pair of elements in opposing relationship while preventing the ends of said longitudinal elements from moving apart from one another.

2. The improvement of claim 1, wherein said step of cutting further comprises cutting the rod a second time in a longitudinal direction perpendicular to said longitudinal extent, so as to obtain a bundle of four elements arranged in a cross and separated by two cuttings, each cutting operation being performed along the median line of the rod.

3. The improvement of claim 2, wherein the step of cutting comprises performing a first cutting operation along a plane containing the median line and the centers of curvature of the rod and performing a second cutting operation along a cylindrical surface perpendicular to said plane and containing the median axis of the rod.

4. The improvement of claim 3, wherein the step of cutting comprises performing the second cutting operation along a portion of the longitudinal extent of the rod away from said head so that the free ends of the elements of the rod located on the same side of this cutting are connected to one another, thus forming two pairs of elements.

5. The improvement of claim 4, wherein said second cutting operation further comprises forming opposing longitudinal slots in the vicinity of each said free end of each pair of elements that coincides with its homologue of the other pair; passing said holding means through the two slots and forming shoulders on opposing ends of said holding means to fix said holding means within said slots and prevent the ends of the pairs of elements from moving apart from one another without, however, opposing their movements longitudinally of one another.

6. A hip prosthesis made by the process as set forth in claim 1.

7. A hip prosthesis made by the process set forth in claim 2.

8. A hip prosthesis made by the process set forth in claim 3.

9. A hip prosthesis made by the process set forth in claim 4.

10. A hip prosthesis made by the process set forth in claim 5.

11. A process for making a hip prosthesis including a bulbous head, a neck extending from said head, a plate connected to the neck opposite the head, and a femoral rod attached to, and extending from, the plate in a direction away from the neck, the process comprising:
    forging said head, neck, plate and rod as a single unitary piece;
    cutting said rod along one longitudinally extending portion thereof from a region near the head to the free end of the rod to form a pair of longitudinal elements;
    forming slots in opposing homologous regions of said longitudinal elements near the free ends thereof;
    inserting a linking element through said slots; and
    deforming opposing ends of said linking element so that each linking element end is retained within each respective slot,
    whereby while movements of said elements longitudinally of one another are permitted during flexing of said elements, the ends of said longitudinal elements are prevented from moving apart from one another.

12. The process of claim 11 wherein said step of cutting comprises cutting along a plane containing the median line, and the centers of curvature, of the rod.

13. The process of claim 11, wherein said step of cutting further comprises cutting said rod a second time along a longitudinally extending portion thereof from a region near said head to a region near the free ends of said longitudinal elements, said second longitudinally extending portion and said one longitudinally extending portion being substantially perpendicular, whereby two pairs of longitudinally extending elements are formed.

14. The process of claim 12, wherein said step of cutting further comprises cutting said rod a second time along a longitudinally extending portion thereof from a region near said head to a region near the free ends of said longitudinal elements, said second longitudinally extending portion and said one longitudinally extending portion being substantially perpendicular, whereby two pairs of longitudinally extending elements are formed.

15. The process of claim 13, wherein said second cutting is made in a plane containing the median axis of the rod.

16. The process of claim 11, wherein said step of deforming comprises forming shoulders on said opposing ends.

17. A hip prosthesis made by the process set forth in claim 11.

18. A hip prosthesis made by the process set forth in claim 13.

19. A hip prosthesis made by the process set forth in claim 16.

* * * * *